(12) United States Patent
Young et al.

(10) Patent No.: US 8,836,200 B2
(45) Date of Patent: Sep. 16, 2014

(54) TORSIONAL MODE ULTRASONIC GENERATOR

(75) Inventors: Michael John Radley Young, South Devon (GB); Stephen Michael Radley Young, South Devon (GB); James Anton Slipszenko, South Devon (GB); Michael James Ede, South Devon (GB)

(73) Assignee: SRA Developments Limited, Ashburton, South Devon (GB)

( * ) Notice: Subject to any disclaimer, the term of this patent is extended or adjusted under 35 U.S.C. 154(b) by 644 days.

(21) Appl. No.: 13/125,999

(22) PCT Filed: Oct. 27, 2009

(86) PCT No.: PCT/GB2009/002562
§ 371 (c)(1),
(2), (4) Date: Aug. 3, 2011

(87) PCT Pub. No.: WO2010/049684
PCT Pub. Date: May 6, 2010

(65) Prior Publication Data
US 2011/0278988 A1     Nov. 17, 2011

(30) Foreign Application Priority Data

Oct. 27, 2008 (GB) .................................. 0819712.1

(51) Int. Cl.
| | | |
|---|---|---|
| *H01L 41/08* | (2006.01) | |
| *A61B 8/12* | (2006.01) | |
| *A61B 17/32* | (2006.01) | |

(52) U.S. Cl.
CPC ............... *A61B 17/320068* (2013.01); *A61B 2017/320096* (2013.01)
USPC ..................................... 310/323.02; 600/439

(58) Field of Classification Search
CPC ............ A61B 17/320068; A61B 2017/320096
USPC .......................................................... 310/334
See application file for complete search history.

(56) References Cited

U.S. PATENT DOCUMENTS 5,116,343 A * 5/1992 Ams et al. ............. 606/128
6,955,680 B2 * 10/2005 Satou et al. ........... 606/169
(Continued)

FOREIGN PATENT DOCUMENTS

| EP | 0 421 285 A1 | 4/1991 |
| EP | 1 323 481 A2 | 7/2003 |

(Continued)

OTHER PUBLICATIONS

Mitskevich, "Sources of High Intensity Ultrasound", edited L.D. Rozenberg.
(Continued)

*Primary Examiner* — J. San Martin
(74) *Attorney, Agent, or Firm* — Heslin Rothenberg Farley & Mesiti P.C.

(57) ABSTRACT

Apparatus (5,50) for generating torsional-mode ultrasonic vibrations comprises a stack of axially-polarized piezo-electric ceramic rings (10) having a torsional converter (1,51,53) mounted coaxially to either one face of the stack or to two opposite faces thereof. Each torsional converter (1,51,53) has a cross-sectional inhomogeneity comprising a plurality of helically-extending grooves (2,55) extending substantially from end to end of the converter. The grooves (2,55) each have a length, measured axially along the converter (1,51,53), of approximately half the wavelength of ultrasonic vibrations therein. When the stack is energized, the stack and the converter (1) or converters (51,53) resonate together in a purely torsional-mode vibration. The apparatus (5,50) is compact and axisymmetric, and is straightforward to incorporate into a simple tool handpiece. The ultrasonic vibrations may be transmitted along a conventional elongate waveguide (3) of a tool to a distal operative tip (35). A very high amplitude torsional oscillation may thus be induced at the operative tip (35) of the tool. Alternatively, a further converter element (32) may be located at a distal end of the waveguide (3) in order partially to convert torsional-mode to longitudinal-mode vibrations for tool operative tips requiring combined-mode oscillations.

24 Claims, 8 Drawing Sheets

(56) References Cited

U.S. PATENT DOCUMENTS

| | | |
|---|---|---|
| 6,984,220 B2 | 1/2006 | Wuchinich |
| 7,651,490 B2 * | 1/2010 | Boukhny et al. .................. 606/1 |
| 2001/0047166 A1 | 11/2001 | Wuchinich |
| 2003/0045887 A1 | 3/2003 | Sakurai |
| 2003/0164659 A1 | 9/2003 | Akihiro et al. |
| 2005/0277869 A1 * | 12/2005 | Boukhny ........................ 604/22 |
| 2006/0004396 A1 * | 1/2006 | Easley et al. .................. 606/169 |
| 2006/0041220 A1 | 2/2006 | Boukhny et al. |
| 2009/0236938 A1 | 9/2009 | Bromfield |

FOREIGN PATENT DOCUMENTS

| | | |
|---|---|---|
| EP | 1 917 936 A1 | 5/2008 |
| GB | 2333709 | 10/1999 |
| WO | WO2009/141618 | 11/2009 |

OTHER PUBLICATIONS

International Search Report of PCT/GB2009/002562 dated Feb. 25, 2010.

* cited by examiner

TORSIONAL MODE ULTRASONIC GENERATOR

This application claims priority to PCT International Application PCT/GB2008/002562 filed on Oct. 27, 2009 which was published on May 6, 2010 as Publication No. WO 2010/049684 A1. The PCT application claims priority to a patent application filed on Oct. 27, 2008 in Great Britain and assigned Patent Application No. GB0819712.1. The entire content of these applications is incorporated herein by reference.

The present invention relates to apparatus for generating torsional-mode ultrasonic vibrations to activate an ultrasonically-vibratable tool, such as a surgical tool. More particularly but not exclusively, it relates to apparatus for generating torsional-mode ultrasonic vibrations, adapted to be incorporated into a handpiece of a surgical tool. The present invention further relates to apparatus for selectively converting torsional-mode ultrasonic vibrations to longitudinal-mode vibrations at an operative end of a tool, particularly a surgical tool.

Work by Young and Young on ultrasonically-vibratable surgical tools has established that in many systems torsional-mode ultrasonic vibrations provide distinct advantages in performance over conventional longitudinal-mode ultrasonic vibrations. Historically, however, generation of longitudinal-mode ultrasonic vibrations has been found to be more straightforward. A coaxially-arranged stack of axially-polarised piezo-electric ceramic elements can easily be induced to produce longitudinal-mode ultrasonic vibrations aligned along the axis of the stack.

One approach to producing torsional-mode ultrasonic vibrations, disclosed in UK Patent No. GB2333709, is to impose such longitudinal-mode vibrations tangentially on a cylindrically-symmetrical conversion horn. This induces torsional-mode vibrations in the horn and in a waveguide extending coaxially therefrom. However, the geometry of the resulting generator may not be convenient, for example when incorporated into a handpiece of a surgical tool. Additionally, improvements are always desirable in the efficiency of conversion of electrical energy into ultrasonic vibrations at the operative tip of a tool. A generator design that is simpler and more economical to construct would also be beneficial.

Initial work by Mitskevich (for example, as published in "Sources of High Intensity Ultrasound, edited L. D. Rozenberg) indicated that the interpolation of an element having cross-sectional inhomogeneities between a stack of axially-polarised piezo-electric elements and an axially-extending waveguide should induce a proportion of torsional-mode vibrations in the waveguide. However, although Mitskevich's proposals were published in the 1960s, it has proved difficult to achieve satisfactory results in practice.

Boukhny, in US Patent Application No. US2006/0041220, and Wuchinich, in U.S. Pat. No. 6,984,220B, have each attempted to implement some of Mitskevich's principles. However, each has used an element having cross-sectional inhomogeneities (CSI element) in order to generate combined longitudinal/torsional vibrational modes in an elongate waveguide. In these applications, the use of combined mode vibrations was deemed desirable (for example, Boukhny had tools for phacoemulsion of cataracts specifically in mind). However, in many surgical and other applications, any longitudinal-mode component of the combined mode is likely to incur the same problems as a pure longitudinal-mode vibration.

Also, ultrasonically-vibratable tools are widely used in laparoscopic surgery. In such situations, it is necessary to shroud or isolate the waveguide to prevent energy being transferred to body tissues anywhere except at the operative tip of the tool. This is both for reasons of patient safety and to ensure that as much of the energy as possible reaches the operative tip of the tool. The shroud is optimally mounted to the waveguide at nodal planes of the vibrations therein, to minimise the vibrational energy transmitted into the shroud. However, in a combined mode vibration, each component will have a different wavelength, so there are likely to be very few or no true nodes. Only a pure torsional-mode vibration or a pure longitudinal-mode vibration is likely to provide a series of suitable nodal mounting points along a waveguide. Similar considerations apply when mounting the generator within a hand-held portion of the tool (handpiece), for which it is important that no vibrations are transferred to the hand of the user.

Bromfield, in US Patent Application No. US2009/0236938, has recently disclosed an attempt to produce a pure torsional-mode vibration from a generator to an extent derived from Mitskevich's principles. This employs two axially-aligned sets of piezo-electric ceramic elements, spaced by an element comprising a brief CSI section. The generator thus has a relatively compact overall shape, and in a narrow frequency band can produce a relatively pure torsional-mode vibration in a waveguide mounted thereto. However, away from this frequency band, it produces a combined mode vibration. The applicant has found that for such arrangements, the efficiency of energy transfer to the distal operative tip of the waveguide is poor. An unacceptably high proportion of the electrical energy delivered to the piezo-electric elements ends up dissipated as heat within the generator, which is both inefficient and potentially unsafe.

It has thus been found to be far from easy to produce an effective torsional-mode ultrasonic generator based on the general principles outlined by Mitskevich. However, if such a generator could be achieved, there should be considerable benefits in respect of the cost, simplicity, ease of manufacture, compactness and convenience of the generator. The highest possible transfer of energy to the operative portion of a tool would of course always be advantageous.

It is hence an object of the present invention to provide a means of generating torsional-mode ultrasonic vibrations, for example to energise a tool comprising an elongate waveguide, that obviates the disadvantages of existing systems while providing some or all of the benefits listed above.

According to a first aspect of the present invention, there is provided apparatus adapted to generate torsional-mode ultrasonic vibrations, comprising a co-axially-aligned array of piezo-electric elements having a substantially co-axially extending first conversion element directly mounted thereto, wherein said first conversion element comprises a cross-sectional inhomogeneity of generally helical symmetry extending from adjacent its proximal end to adjacent its distal end.

Elongate waveguide means may be mounted or mountable to said first conversion element.

Said waveguide means may extend substantially coaxially from the first conversion element.

Preferably, said cross-sectional inhomogeneity has an axial length of at least $\lambda_T/2$, where $\lambda_T$ is the wavelength of ultrasonic vibrations within the conversion element.

More preferably, said cross-sectional inhomogeneity has an axial length corresponding substantially to $\lambda_T/2$.

Advantageously, the cross-sectional inhomogeneity extends along at least three-quarters of the length of the first conversion element, optionally along at least nine-tenths of the length thereof.

The first conversion element may comprise a proximal homogeneous portion extending between the cross-sectional inhomogeneity and the proximal end of the conversion element, said homogeneous portion having an axial length of $\lambda_T/10$ or less, optionally of $\lambda_T/20$ or less.

The first conversion element may comprise a distal homogeneous portion extending between the cross-sectional inhomogeneity and the distal end of the conversion element, said homogeneous portion having an axial length of $\lambda_T/10$ or less, optionally of $\lambda_T/20$ or less.

Said cross-sectional inhomogeneity preferably comprises a plurality of helically-extending groove means, extending substantially parallelly each to the others from adjacent the proximal end of the first conversion element to adjacent its distal end.

There may be an even number of said groove means, optionally two or four.

Each groove means may have a depth of between 10% and 40% of an overall diameter of the conversion element, optionally between 20% and 40% thereof, or between 20% and 30% thereof.

Each groove means may have a width of between 2% and 20% of an overall diameter of the conversion element, optionally between 3% and 14% thereof, or between 10% and 14% thereof.

Each groove means may extend helically between its respective proximal and distal ends for substantially a complete rotation around a circumference of the conversion element.

In a preferred embodiment, the apparatus comprises a second conversion element extending substantially coaxially from the array of piezo-electric elements, remotely from the first conversion element.

Said second conversion element may be substantially similar to the first.

The second conversion element may be mounted directly to the first, optionally by mounting means extending through or around the array of piezo-electric elements.

According to a second aspect of the present invention, there is provided apparatus adapted to generate torsional-mode ultrasonic vibrations, comprising a co-axially-aligned array of piezo-electric elements having a substantially co-axially extending first conversion element mounted thereto, wherein said first conversion element comprises a cross-sectional inhomogeneity of generally helical symmetry having an axial length corresponding substantially to $\lambda_T/2$, where $\lambda_T$ is the wavelength of ultrasonic vibrations within the conversion element.

Preferably, said cross-sectional inhomogeneity extends from adjacent a proximal end of the first conversion element to adjacent its distal end.

In a preferred embodiment, the apparatus comprises a second conversion element extending substantially coaxially from the array of piezo-electric elements, remotely from the first conversion element.

Said second conversion element may be substantially similar to the first.

The second conversion element may be mounted directly to the first, optionally by mounting means extending through or around the array of piezo-electric elements.

According to a third aspect of the present invention, there is provided apparatus adapted to generate torsional mode ultrasonic vibrations, comprising a co-axially aligned array of axially-polarised piezo-electric elements having a substantially co-axially extending first conversion element mounted thereto, wherein said first conversion element comprises a cross-sectional inhomogeneity of generally helical symmetry, and wherein energising of the array of piezo-electric elements induces a torsional-mode ultrasonic vibration in both the first conversion element and the array of axially-polarised piezo-electric elements.

Preferably, the apparatus further comprises a second conversion element substantially identical to the first conversion element and extending substantially coaxially from a face of the array opposite the first conversion element.

In any of the above aspects, the apparatus may be provided with isolating mounting means adapted to receive casing means therefor, said isolating mounting means being mounted to the apparatus at a nodal plane located within the array of piezo-electric elements.

Said isolating mounting means may be mounted adjacent a midpoint of said array.

According to a fourth aspect of the present invention, there is provided ultrasonically vibratable tool means comprising means to generate ultrasonic vibrations operatively connected to elongate waveguide means extending to an operative distal tip of the tool means, wherein the waveguide means comprises a cross-sectional inhomogeneity having a generally helical symmetry located adjacent said distal tip.

Said cross-sectional inhomogeneity may be adapted to convert torsional-mode ultrasonic vibrations in the waveguide means at least partially into longitudinal-mode ultrasonic vibrations in the operative distal tip.

Said cross-sectional inhomogeneity may be adapted to convert longitudinal-mode ultrasonic vibrations in the waveguide means at least partially into torsional-mode ultrasonic vibrations in the operative distal tip.

Said cross-sectional inhomogeneity may comprise a plurality of helically-extending groove means, each extending parallelly to the others between a proximal end of the cross-sectional inhomogeneity and a distal end thereof.

The means to generate ultrasonic vibrations may comprise apparatus for generating torsional-mode ultrasonic vibrations as described in any one of the first to third aspects above.

Embodiments of the present invention will now be more particularly described by way of example and with reference to the accompanying drawings, in which.

Figure 1A:
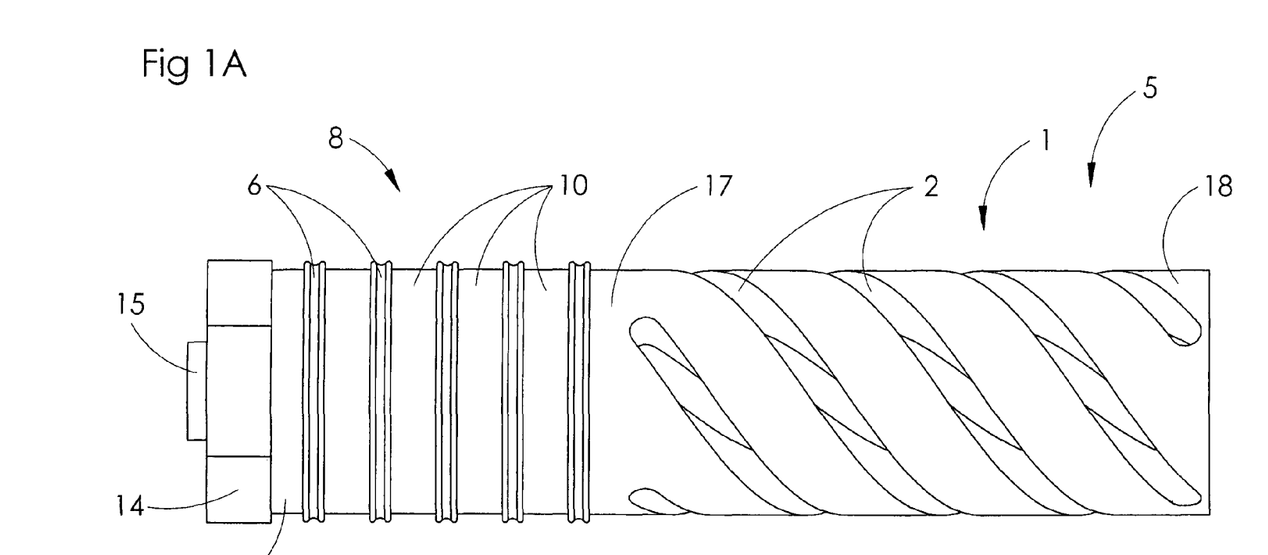
FIG. 1A is a side elevation of a first transducer unit embodying the present invention.
Figure 1B:
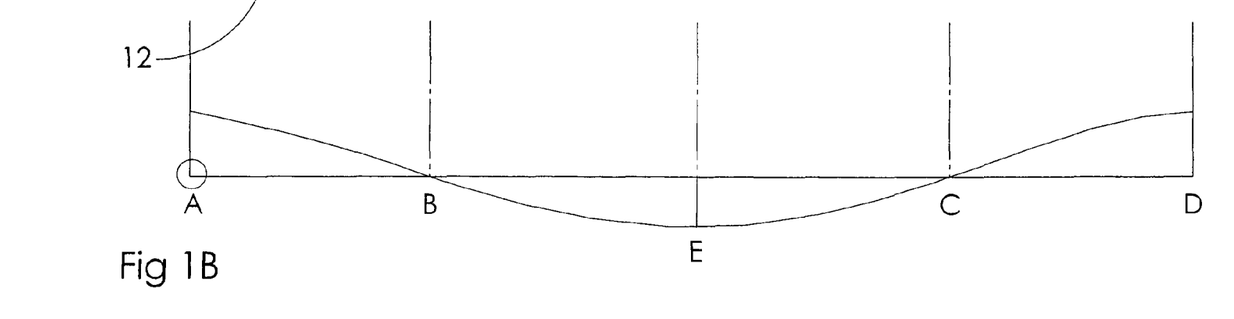
FIG. 1B is a schematic representation of a displacement amplitude of ultrasonic vibrations along the first transducer unit of FIG. 1A, in operation.

Referring now to the Figures, and to FIGS. 1A and 1B in particular, a first transducer unit 5 comprises a substantially conventional piezo-electric ceramic stack 8 and an output section 1 comprising a cross-sectional inhomogeneity (CSI), mounted to a distal face of the stack 8.

The stack 8 comprises four axially-polarised/thickness-polarised piezo-electric transducer (PZT) rings 10, separated by five conductive electrodes 6, which may be brass rings or beryllium-copper shims. The PZT rings 10 and the electrodes 6 are held in compression between the output section 1 and a washer 12, secured by a nut 14 threaded on to a proximal end of a spigot 15, which extends coaxially through the stack 8 from a proximal end of the output section 1.

The PZT rings 10 are electrically connected as two parallel pairs, with end and central electrodes 6 at a low potential and alternating connections to a high tension (HT) drive voltage, which is typically of sinusoidal form.

The stack 8 thus has a substantially cylindrical symmetry. The output section 1 is also substantially cylindrical, extends coaxially from the distal face of the stack 8, and has substantially the same diameter as the stack 8.

If the output section 1 were no more than a plain cylindrical element, then this geometry, with thickness-polarised (i.e. axially-polarised) rings 10, would generate purely longitudinal ultrasonic vibrations directed axially along the output section 1. Such a longitudinal-mode (or compression-mode) stack transducer would be a relatively inexpensive unit and straightforward to produce.

However, with the output section 1 comprising a suitable cross-sectional inhomogeneity, as shown, the behaviour of the first transducer unit 5 is radically different. The CSI comprises four helical grooves 2, extending from adjacent a proximal end of the output section 1 substantially to its distal end. The grooves 2 are equally spaced around the circumference of the output section 1, and each helical groove 2 extends through 360° around the output section 1 from end to end. The grooves 2 extend along about 90% of the overall length of the output section 1, measured axially. The ungrooved proximal portion 17 and distal portion 18 of the output section 1 are as short as possible, consistent with providing adequate strength and a secure flat contact surface for marrying adjacent elements thereto.

For an output section 1 of overall diameter fifteen millimeters, the spiral grooves 2 should be from two to five millimeters deep; ideally, the groove 2 depth should be between 20% and 40% of the diameter of the output section 1. The groove 2 width should be between 0.45 mm and 3 mm, ideally between 3% and 14% of the diameter of the output section 1. Groove 2 widths, of 1.5-2 mm are most straightforward to manufacture and are highly effective.

With an output section 1 of this structure securely coupled to the stack 8, conversion from longitudinal-mode ultrasonic vibrations to torsional-mode vibrations is complete. Indeed, contrary to conventional wisdom and to the behaviour of other attempts to produce CSI-based conversion arrangements, once energised the entire stack 8 rapidly enters a purely torsional vibrational mode with no trace of a longitudinal component, despite both the polarisation of the rings 10 and the applied electrical potential being solely axially-aligned.

Thus, as shown in FIG. 1B, a single purely torsional vibrational mode extends throughout the first transducer unit 5. There is maximum rotational displacement amplitude at the proximal end of the unit 5 (point A), at the distal end of the unit (point D) and roughly adjacent a proximal end of the grooves 2 (point E). There are nodal planes at a midpoint of the stack 8 (point B) and adjacent a midpoint of the grooves 2 (point C), at which points the rotational displacement amplitude is zero or close to zero. (This has been confirmed by microscopic examination of fine powder films dusted on to the end faces and cylindrical surfaces of an activated transducer unit 5. This examination also confirmed the absence of any longitudinal vibrational components at either end, points A and D).

For a well-tuned system, the grooves 2 each extend a distance 412 measured axially along the output section 1, where $\lambda_T$ is the wavelength of the torsional vibrations set up in the output section 1. It has been found that finite element analysis (FEA) is a preferred method for rapidly establishing the appropriate parameters, although other approaches may also provide results sufficiently close for subsequent fine-tuning.

It is found that the lengths of the proximal 17 and distal 18 ungrooved portions are also best governed by the wavelength $\lambda_T$ of the vibrations therein. Each ungrooved portion should be less than $\lambda_T/10$ long, and ideally less than $\lambda_T/20$ long, measured axially. Not only would longer ungrooved portions 17, 18 represent wasted material, but they would also tend to weaken the vibrational coupling between the stack 8 and the grooved portion of the output section 1, probably leading to only partial conversion of longitudinal to torsional-mode vibrations.

The transducer unit 5 as a whole is compact and axisymmetric. It is easy to incorporate into a tool handpiece of convenient size and shape, particularly since there are two nodal planes at which a casing may conveniently be mounted to the unit 5 in vibrational isolation.

Figure 2:
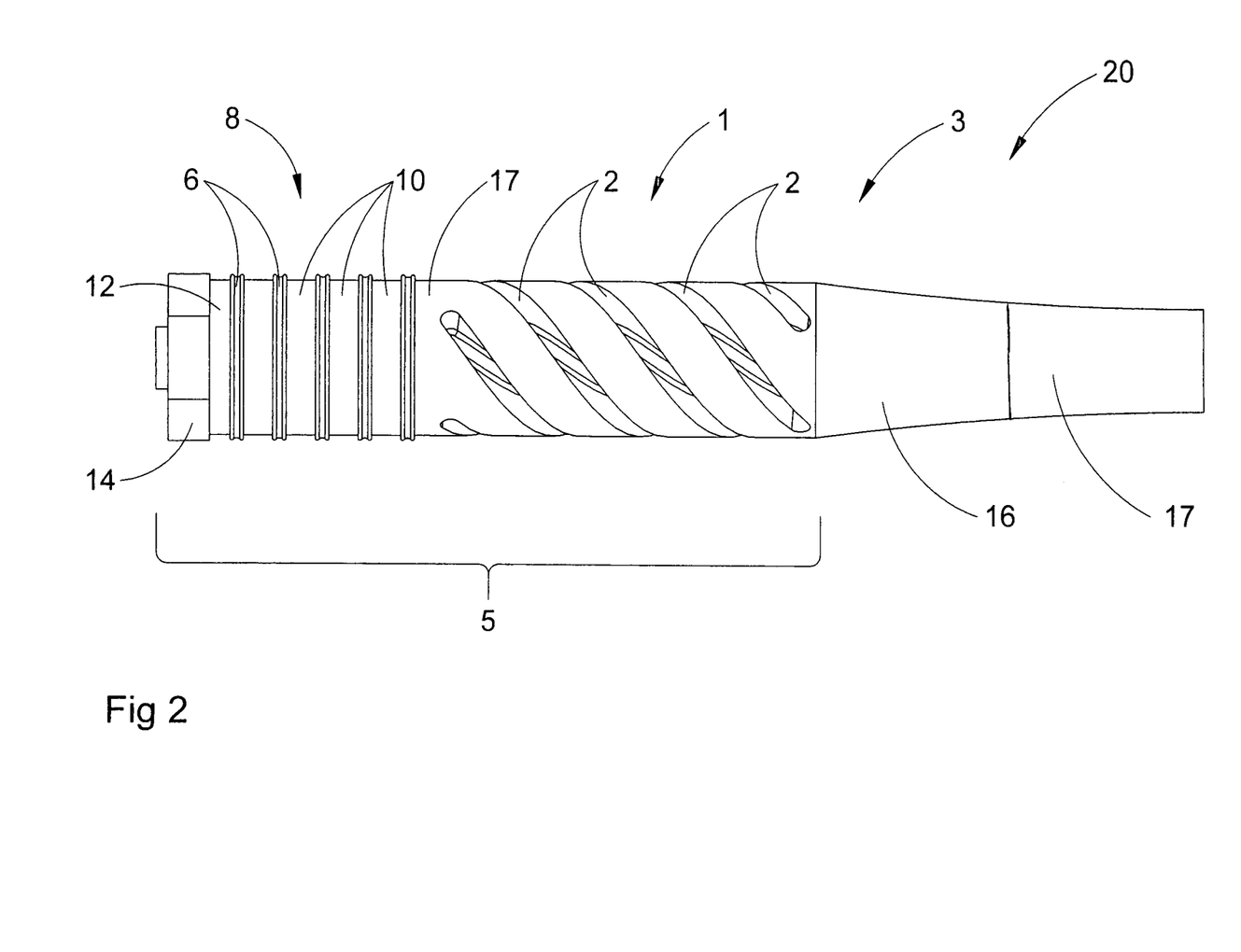
FIG. 2 is a side elevation of a second transducer unit embodying the present invention.

FIG. 2 shows a second transducer unit 20, which comprises a transducer unit 5 very similar to the first transducer unit 5 shown in FIG. 1A, with the addition of a half-wave focussing horn 3, comprising a tapering input portion 16 mounted directly to the distal face of the output section 1 and a parallel/cylindrical output portion 17 extending coaxially distally from the input portion 16.

Focussing horns 3 of this type are useful for amplifying torsional-mode vibrations as they are transmitted into an elongate narrow cylindrical coaxial waveguide, of the form typically used in a surgical tool, such as a laparoscopic tool for cutting and/or coagulating body tissues, blood vessels and the like.

Figures 3A, 3B:
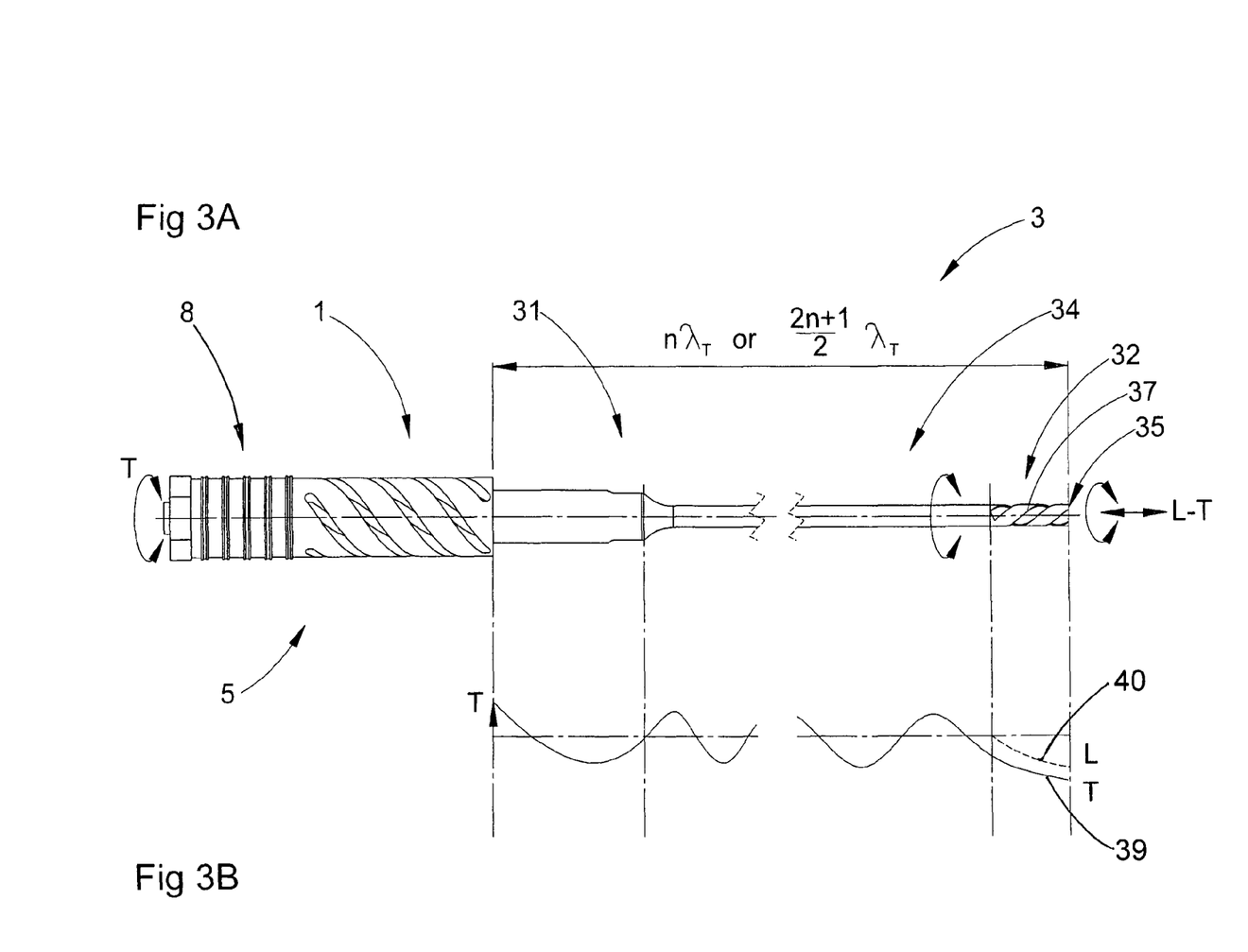
FIG. 3A is a side elevation of an operative portion of a surgical tool embodying the present invention.
FIG. 3B is a schematic representation of a displacement amplitude of ultrasonic vibrations along a waveguide of the surgical tool shown in FIG. 3A, in operation.

An example of such a tool is shown in FIG. 3. A horn 31 is mounted coaxially to a distal face of a first transducer unit 5, which is substantially the same as that shown in FIG. 1A. A thin, elongate, cylindrical waveguide 34 extends from the horn 31 to an end effector at a distal tip 35 of the tool. The waveguide 34 and horn 31 between them extend either $n\lambda_T$ or $(2n+1) \lambda_T/2$, where $\lambda_T$ is the wavelength of the torsional ultrasonic vibrations therein. Thus, the displacement amplitude is at a maximum at the distal tip 35 (see FIG. 3B). This has an additional benefit that there are a series of nodes along the waveguide 34, at predictable positions, at which one may mount a shroud to encase the waveguide. Being at a node, minimal vibrational energy is dissipated through the respective mounting arrangements into the shroud (and hence, potentially, into tissues contacting the shroud).

The end effector itself may be of any desired form that is operable by torsional-mode ultrasonic vibrations (see for example UK Patent No. GB2333709 and many others having inventors in common with the present application). No end-effector is hence shown in FIG. 3A, for simplicity.

However, there are also forms of end-effector for which combinations of longitudinal-mode and torsional-mode excitation might be desirable. As mentioned above, if a combined-mode ultrasonic vibration is propagated along an elongate waveguide, nodes of the torsional-mode component are highly unlikely to coincide with nodes of the longitudinal-mode component. Thus, mounting shrouds or other components of the tool to the waveguide is likely to be a major problem, since vibrational energy of either or both components is liable to be lost through the mountings. It is also likely to be difficult to arrange for both components to produce a maximum amplitude at or near the end-effector.

Figure 3C:
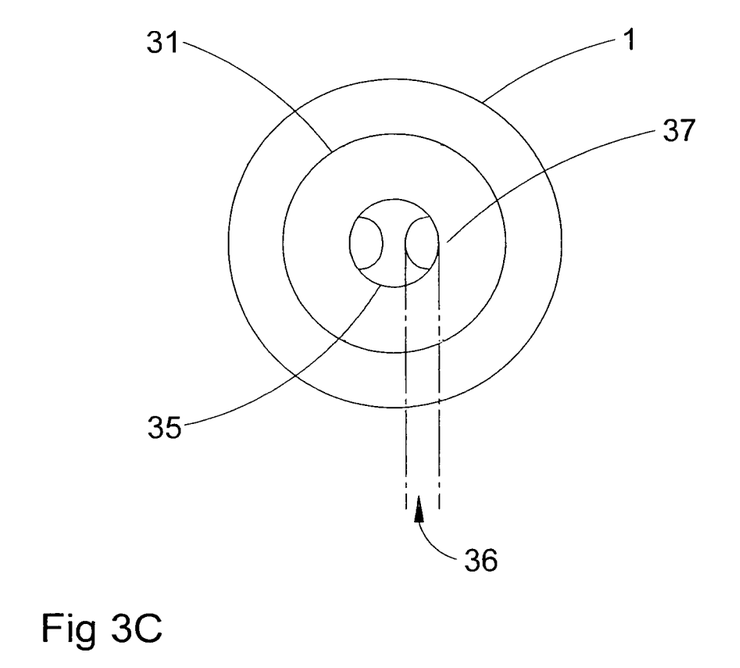
FIG. 3C is a distal end elevation of the surgical tool shown in FIG. 3A.

In such cases, the incorporation of a further cross-sectional inhomogeneity (CSI) feature is likely to be of benefit, as shown in FIG. 3A. A short CSI portion 32 is disposed at a distal end of the waveguide 34, adjacent the distal tip 35. A series of helical grooves 37 extend around the CSI portion 32, each having a depth 36 (see FIG. 3C).

When a pure torsional-mode vibration is propagated along the waveguide 34, the distal CSI portion 32 converts a portion of the torsional-mode displacement wave to a longitudinal-mode compression wave at the distal tip 35 (see the torsional wave 39 and the dashed longitudinal wave 40 in FIG. 3B). A remainder of the waveguide 34 remains resonant in a pure torsional mode, avoiding problems with isolation along its length. The proportion of the torsional-mode energy transformed to longitudinal-mode depends on the depth 36 of the grooves 37 and the pitch of the helical profile of the grooves 37. Shallower grooves 37 favour the torsional-mode component, while deeper grooves 37 increase the transformation to longitudinal-mode.

This partial transformation of torsional-mode to longitudinal-mode vibrations would not only be useful in conjunction with torsional-mode transducer units 5 embodying the present invention, but could also potentially be applied to waveguides energised by known torsional-mode ultrasonic generators, such as those described in UK Patent No. GB2333709 and others.

While partial longitudinal-mode to torsional-mode conversion, using CSIs adjacent a proximal end of a waveguide, has previously been demonstrated by Boukhny, Wuchinich and others (see above), it is believed that this is the first instance of torsional-mode to longitudinal-mode conversion with a CSI, and the first instance of mode conversion at a distal end of the waveguide.

A third transducer unit 50 embodying the present invention is shown in FIGS. 4A to 4D and 5. Again, a conventional axial-mode PZT stack is provided comprising four thickness-polarised PZT rings 10, with five interleaved electrodes 52, all but one 56 of conventional form. However, this third transducer unit 50 is provided with two CSIs, in the form of two spring torsional converters 51, 53 (the output section 1 of the first transducer unit 5 may also be considered as a spring torsional converter).

Figure 4A:
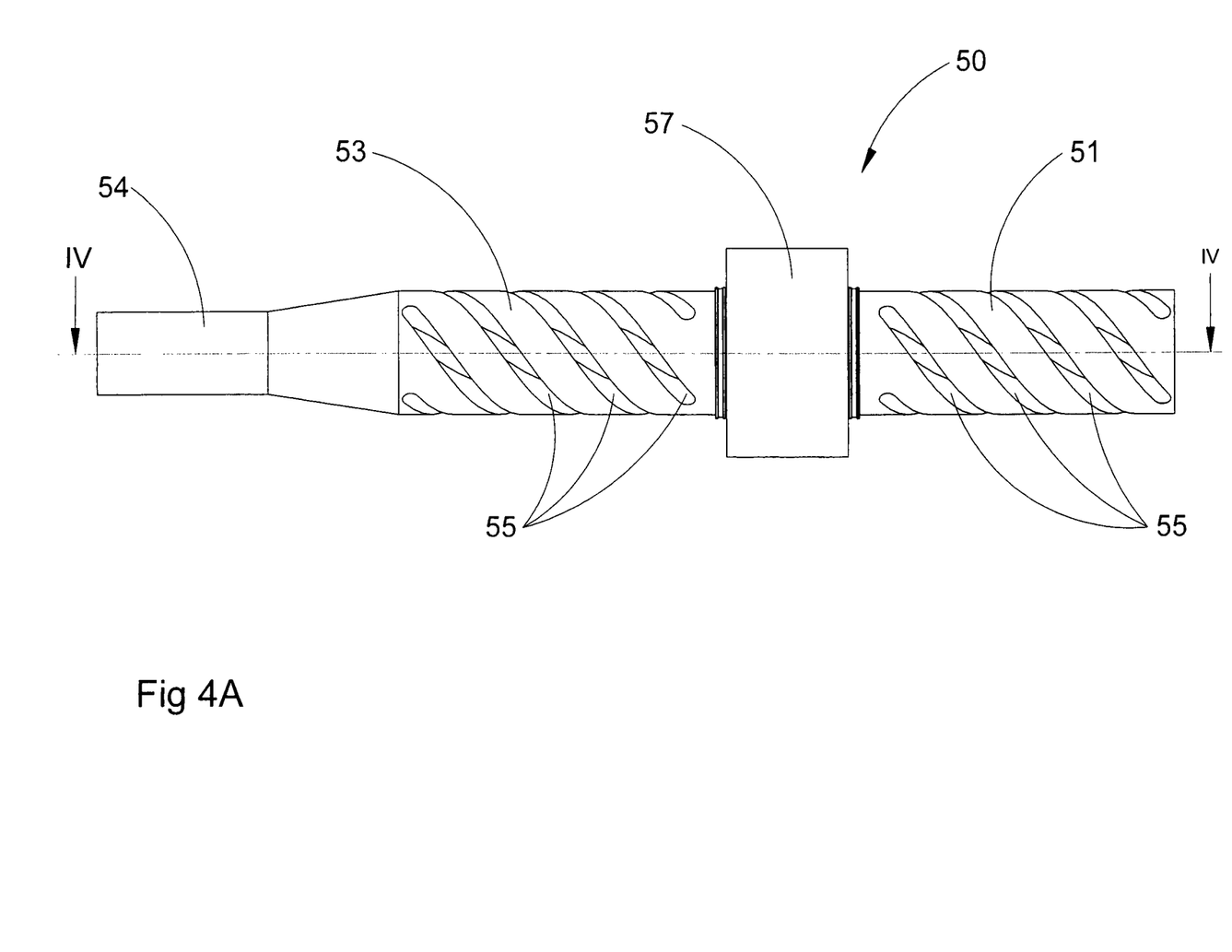
FIG. 4A is a side elevation of a third transducer unit embodying the present invention.
Figure 4B:
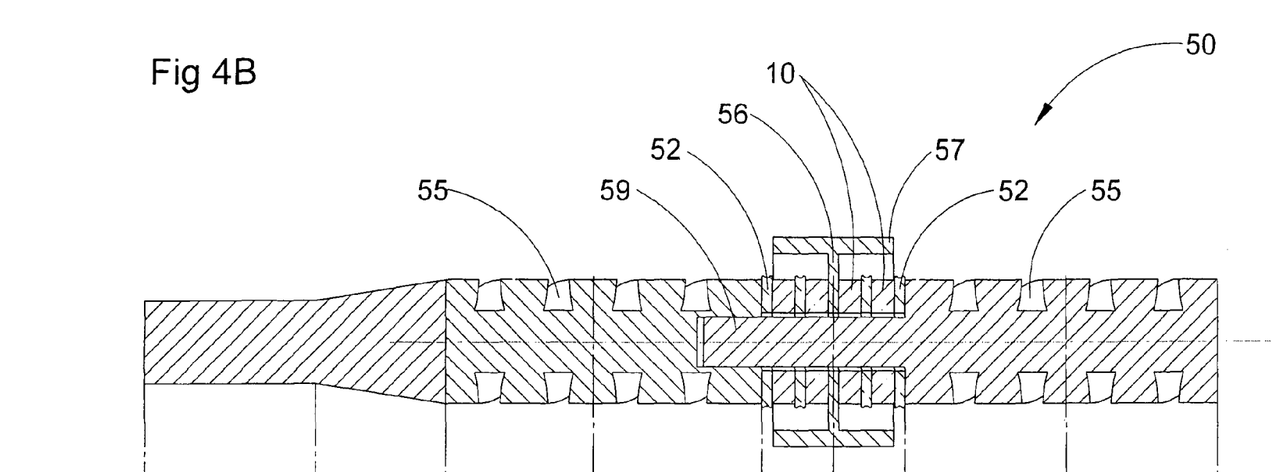
FIG. 4B is a cross-sectional elevation of the third transducer unit shown in FIG. 4A, taken along the line IV-IV.

A distal spring torsional converter 53 is mounted to a distal face of the PZT stack, and drives a conventional torsional horn 54 extending coaxially from its distal end. The distal spring torsional converter 53 is provided with four equally-spaced helical grooves 53 extending for a distance $\lambda_T/2$ along its length and having a pitch of 360° from end to end, as for the output section 1 of the first transducer unit 5.

The third transducer unit 50 also comprises a proximal spring torsional converter 51, which is mounted to extend coaxially from a proximal face of the PZT stack. A spigot 59 extends from the proximal converter 51, coaxially through the PZT rings 10 of the stack and into a cooperatively threaded socket in the distal converter 53. The two converters 51, 53 thus also act as front and back plates to compress the PZT stack between them.

This geometry has several benefits. One is that the transducer comprising the stack of PZT rings 10 and the two converters 51, 53 is wholly symmetrical, and there is a fixed nodal plane at the midpoint of the stack. A central one of the electrodes 56 may thus be extended radially outwardly to double as a nodal mounting element. This provides substantially complete acoustic isolation. An isolating sleeve 57 is formed as part of the nodal mounting element/electrode 56, to which a handpiece casing may safely and conveniently be mounted in turn.

The mounting of the proximal converter 51 to the distal converter 53 adds further torsional gain to the distal converter 53, compared with the arrangement of the first transducer unit 5.

The output of the third transducer unit 50 is (as for the first unit 5) a pure torsional-mode ultrasonic vibration, and the entire third transducer unit 50 again undergoes a single torsional-mode vibration, including the stack of axially-driven, thickness-polarised PZT rings 10. However, the efficiency of energy transfer to a waveguide, in the form of torsional-mode vibrations, is even greater than for the first unit 5.

Figure 4C:
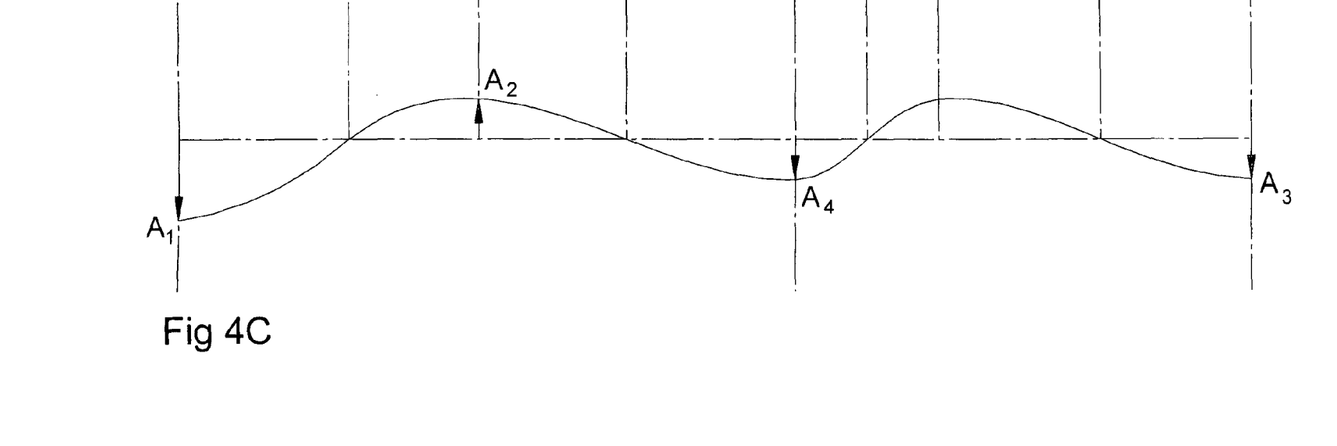
FIG. 4C is a schematic representation of a displacement amplitude of ultrasonic vibrations along the third transducer unit shown in FIGS. 4A and 4B, in operation.
Figure 4D:
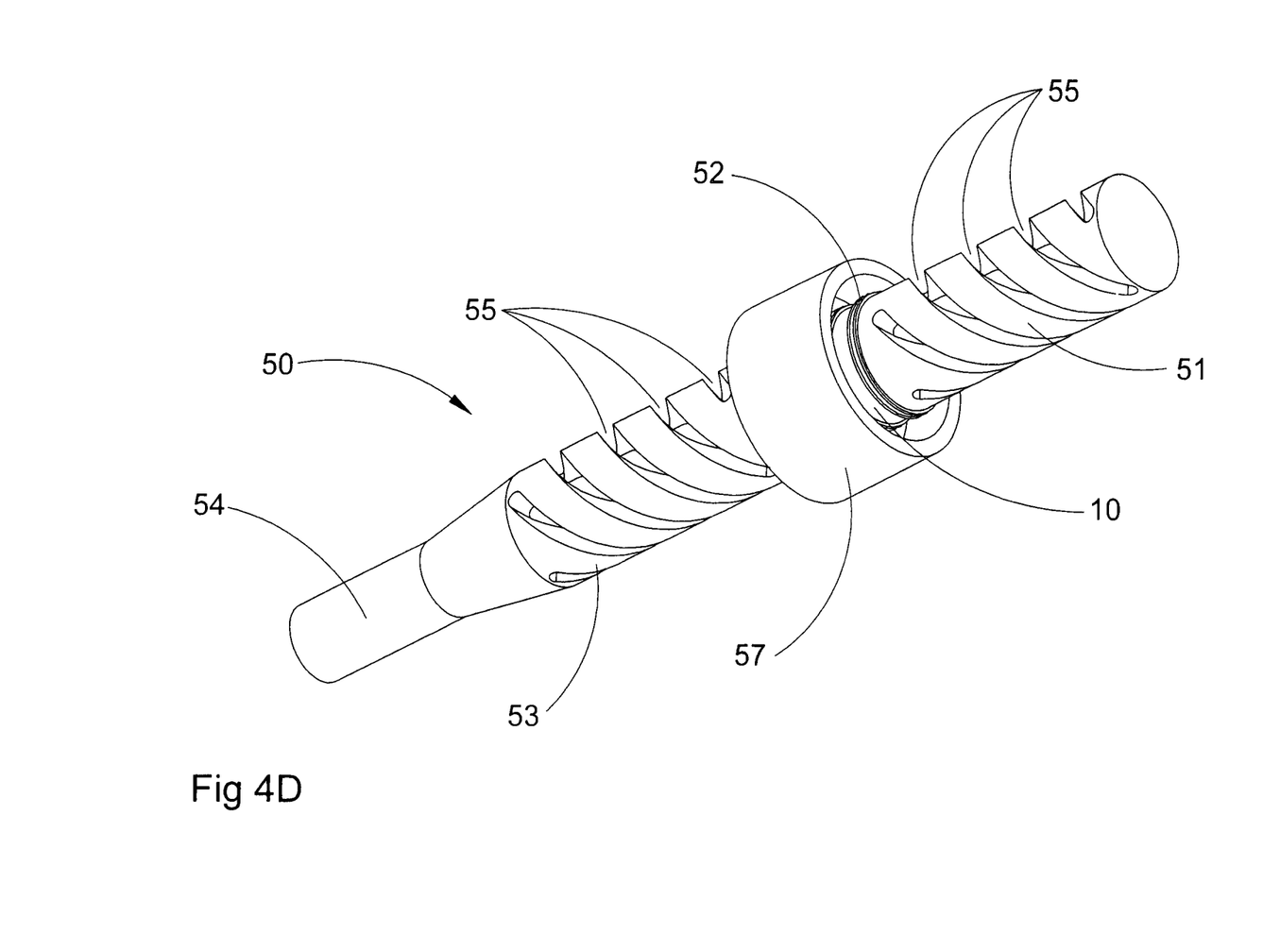
FIG. 4D is an isometric view of the third transducer unit shown in FIGS. 4A and 4B.
Figure 5:
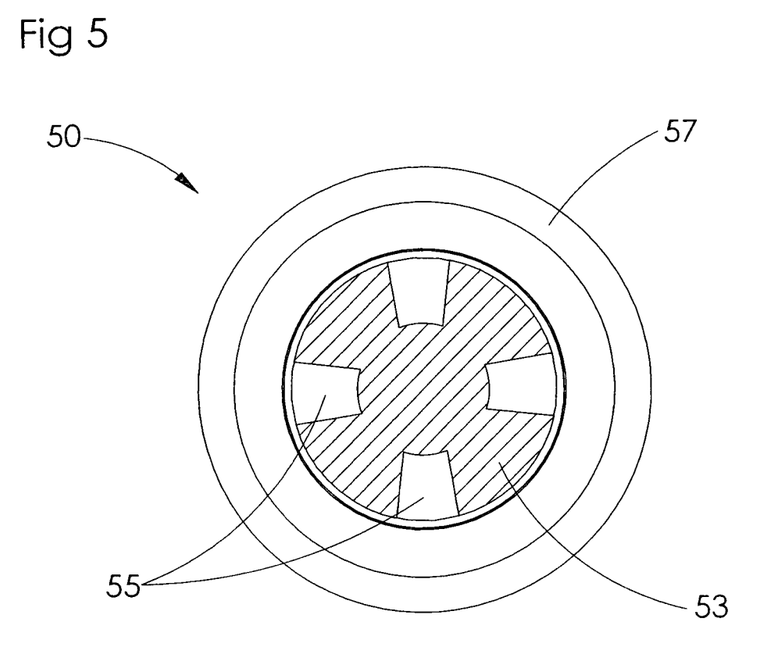
FIG. 5 is a radial cross-sectional view through an output section of the third transducer unit shown in FIGS. 4A, 4B and 4D.

Referring to FIG. 4C, a trace 60 of the displacement amplitude along the third transducer unit 50 is shown. The proximal 51 and distal 53 converters each have a length substantially corresponding to half the wavelength of the torsional mode vibrations therein (as in the case of the output section 1 of the first transducer unit 5, the lengths of the respective ungrooved portions of the converters 51, 53 are kept to a minimum, ideally less than one tenth or even one twentieth of a wavelength). The stack of PZT rings 10 also has a length corresponding to half the (shorter) wavelength of the torsional-mode vibrations therein, and the horn 54 is also tuned to be half a wavelength long. Thus, there are maximum displacement amplitudes at the proximal end of the proximal converter 51 ($A_3$), the distal face of the stack ($A_4$), the distal end of the distal converter 53/proximal end of the horn 54 ($A_2$) and at the distal end of the horn 54 ($A_1$). The gains produced at these junctions are such that $A_1 > A_2 > A_3 > A_4$, (NB: the relative amplitudes shown in FIG. 4C are not to scale; latest results indicate that $A_2$ is approximately twice $A_3$). Thus, a very high proportion of the energy supplied to the stack may be projected as torsional-mode ultrasonic vibrations from the distal end of the horn 54 into a conventional waveguide or the like, coaxially extending therefrom.

It is found that for a four-millimeter diameter distal end-effector mounted to such a waveguide, a pure torsional-mode ultrasonic vibration can be delivered to the end-effector which results in a displacement amplitude, measured around the circumference of the end-effector, of 200 μm. This represents much more efficient and effective energy transfer than can be achieved with existing systems, in addition to the benefits of torsional-mode transmission described above.

For the third transducer unit 50, it should be noted that the sets of helical grooves 55 in the proximal 51 and distal 53 converters should be correctly phased as shown, to maximise the overall system gain and to avoid the generation of unwanted longitudinal-mode components. If the helical grooves 55 were aligned in opposite senses, then their effects would probably cancel out.

It is interesting that the present invention represents a further example, in addition to that disclosed in the present applicant's co-pending PCT Application No. PCT/GB2009/001281, of how it is possible, given a creative choice of additional mechanical elements, to induce simple, essentially conventional axially-polarised PZT rings and stacks to vibrate in a non-axial mode and to produce efficiently a high-amplitude vibrational output in that non-axial mode. In the above reference, a flexural mode can be induced from an ostensibly axially-driven stack, while in the present application, it is a torsional mode that can be generated in place of the anticipated longitudinal/extensional mode. Normally, forcing such a stack to vibrate in another mode would be very inefficient, but it is now possible to deliver efficiently a high displacement output from a simple and economical stack of thickness-polarised PZT elements.

The invention claimed is:

1. Apparatus adapted to generate pure torsional-mode ultrasonic vibrations, comprising a co-axially aligned array of piezo-electric elements having a distal face, and a substantially co-axially extending first conversion element having a proximal end directly mounted to the distal face of the array, wherein said first conversion element comprises a cross-sectional inhomogeneity of generally helical symmetry extending from adjacent the proximal end of the first conversion element to adjacent a distal end of the first conversion element.

2. Apparatus as claim in claim 1, wherein said cross-sectional inhomogeneity has an axial length of at least $\lambda_T/2$, where $\lambda_T$ is the wavelength of ultrasonic vibrations with the first conversion element.

3. Apparatus as claimed in claim 1, wherein said cross-sectional inhomogeneity has an axial length corresponding substantially to $\lambda_T/2$ where $\lambda_T$ is the wavelength of ultrasonic vibrations within the first conversion element.

4. Apparatus as claimed in claim 1, wherein the cross-sectional inhomogeneity extends along at least three-quarters of a full length of the first conversion element.

5. Apparatus as claimed in claim 1, wherein the first conversion element comprises a proximal homogeneous portion extending between the cross-sectional inhomogeneity and the proximal end of the first conversion element, said proximal homogeneous portion having an axial length of $\lambda_T/10$ or less, where $\lambda_T$ is the wavelength of ultrasonic vibrations within the first conversion element.

6. Apparatus as claimed in claim 1, wherein the first conversion element comprises a distal homogeneous portion extending between the cross-sectional inhomogeneity and the distal end of the conversion element, said homogeneous portion having an axial length of $\lambda_T/10$ or less, where $\lambda_T$ is the wavelength of ultrasonic vibrations within the first conversion element.

7. Apparatus as claimed in claim 1, wherein said cross-sectional inhomogeneity comprises a plurality of helically-extending grooves, extending substantially parallelly to each other from adjacent the proximal end of the first conversion element to adjacent the distal end of the first conversion element.

8. Apparatus as claimed in claim 7, wherein each groove has a depth of between 10% and 40% of an overall diameter of the first conversion element.

9. Apparatus as claimed in claim 7, wherein each groove has a width of between 2% and 20% of an overall diameter of the first conversion element.

10. Apparatus as claimed in claim 7, wherein each groove extends helically between its respective proximal and distal ends for substantially a complete rotation around a circumference of the first conversion element.

11. Apparatus as claimed in claim 1, comprising a second conversion element extending substantially coaxially from the array of piezo-electric elements, remotely from the first conversion element.

12. Apparatus as claimed in claim 11, wherein said second conversion element is substantially similar to the first conversion element.

13. Apparatus as claimed in claim 1, wherein the cross-sectional inhomogeneity extends along at least nine-tenths of a full length of the first conversion element.

14. Apparatus as claimed in claim 1, wherein, when the array is energized, a single purely torsional mode extends throughout the array and the first conversion element.

15. Apparatus adapted to generate pure torsional-mode ultrasonic vibrations, comprising a co-axially aligned array of piezo-electric elements having a substantially co-axially extending first conversion element mounted thereto, wherein said first conversion element comprises a cross-sectional inhomogeneity of generally helical symmetry having an axial length corresponding substantially to $\lambda_T/2$, where $\lambda_T$ is the wavelength of ultrasonic vibrations within the first conversion element.

16. Apparatus as claimed in claim 15, wherein said cross-sectional inhomogeneity extends from adjacent a proximal end of the first conversion element to adjacent a distal end of the first conversion element.

17. Apparatus as claimed in claim 15, comprising a second conversion element extending substantially coaxially from the array of piezo-electric elements, remotely from the first conversion element.

18. Apparatus as claimed in claim 15, wherein the second conversion element is substantially similar to the first conversion element.

19. Apparatus adapted to generate pure torsional mode ultrasonic vibrations, comprising a co-axially aligned array of axially-polarised piezo-electric elements having a substantially co-axially extending first conversion element mounted thereto, wherein said first conversion element comprises a cross-sectional inhomogeneity of generally helical symmetry, and wherein energising the array of piezo-electric elements induces a pure torsional-mode ultrasonic vibration in both the first conversion element and the array of axially-polarised piezo-electric elements.

20. Apparatus as claimed in claim 19, further comprising a second conversion element substantially identical to the first conversion element and extending substantially coaxially from a face of the array of piezo-electric elements opposite the first conversion element.

21. Apparatus as claimed in claim 19, provided with isolating mountings adapted to receive a casing for the apparatus, said isolating mountings being mounted to the apparatus at a nodal plane located within the array of piezo-electric elements.

22. An ultrasonically vibratable tool comprising means to generate ultrasonic vibrations operatively connected to an elongate waveguide extending to an operative distal tip of the tool, wherein the waveguide comprises a cross-sectional inhomogeneity having a generally helical symmetry located adjacent said distal tip of the tool, said cross-sectional inhomogeneity being adapted to convert torsional-mode ultrasonic vibrations in the waveguide at least partially into longitudinal-mode ultrasonic vibrations at the operative distal tip of the tool.

23. A tool as claimed in claim 22, wherein said cross-sectional inhomogeneity comprises a plurality of helically-extending grooves, extending parallelly to each other between a proximal end of the cross-sectional inhomogeneity and a distal end of the cross-sectional inhomogeneity.

24. A tool as claimed in claim 22, wherein the means to generate ultrasonic vibrations comprises apparatus for generating torsional-mode ultrasonic vibrations as claimed in claim 1.

* * * * *

UNITED STATES PATENT AND TRADEMARK OFFICE
CERTIFICATE OF CORRECTION

PATENT NO. : 8,836,200 B2  
APPLICATION NO. : 13/125999  
DATED : September 16, 2014  
INVENTOR(S) : Young et al.

Page 1 of 1

It is certified that error appears in the above-identified patent and that said Letters Patent is hereby corrected as shown below:

In the Claims

Column 9, Line 21: Claim 2, Delete "with" and insert --within--

Signed and Sealed this
Sixteenth Day of December, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,836,200 B2 | Page 1 of 1 |
| APPLICATION NO. | : 13/125999 | |
| DATED | : September 16, 2014 | |
| INVENTOR(S) | : Young et al. | |

It is certified that error appears in the above-identified patent and that said Letters Patent is hereby corrected as shown below:

In the Claims

Column 10, Line 23: Claim 18, Delete "claim 15" and insert --claim 17--

Signed and Sealed this
Twentieth Day of January, 2015

Michelle K. Lee
*Deputy Director of the United States Patent and Trademark Office*